US00PP17838P2

(12) United States Plant Patent
van Zanten

(10) Patent No.: US PP17,838 P2
(45) Date of Patent: Jun. 26, 2007

(54) ***CHRYSANTHEMUM* PLANT NAMED 'GG 6501'**

(50) Latin Name: *Chrysanthemum grandiflora*
Varietal Denomination: GG 6501

(75) Inventor: Leo van Zanten, Oxnard, CA (US)

(73) Assignee: Grolink Corporation, Oxnard, CA (US)

( * ) Notice: Subject to any disclaimer, the term of this patent is extended or adjusted under 35 U.S.C. 154(b) by 0 days.

(21) Appl. No.: 11/236,976

(22) Filed: Sep. 28, 2005

(51) Int. Cl.
*A01H 5/00* (2006.01)

(52) U.S. Cl. ..... Plt./290

(58) Field of Classification Search ..... Plt./290
See application file for complete search history.

*Primary Examiner*—Anne Marie Grunberg
*Assistant Examiner*—Georgia Helmer

(57) ABSTRACT

A new and distinct *Chrysanthemum* plant cultivar is disclosed, characterized by large daisy type inflorescences, consistent flowering response to short days, blooming consistently after 50 to 55 days of short day length, bi color orange and yellow ray florets, moderate to compact growth habit and a postharvest longevity of an average of 35 days.

1 Drawing Sheet

Latin name of the genus and species: *Chrysanthemum grandiflora* 'GG 6501'.

BACKGROUND OF THE INVENTION

The new cultivar 'GG 6501' is a product of a naturally occurring, single branch mutation of the parent *Chrysanthemum* plant variety 'GG 450' (not patented) which is an undistributed proprietary cultivar. The new cultivar was discovered and selected by Leo van Zanten in August 2003 in Oxnard, Calif.

Asexual reproduction of the new cultivar 'GG 6501' by terminal cuttings and tissue culture was performed in Oxnard, Calif. and Carpinteria, Calif., and has shown that the unique features of this new cultivar are stable and reproduced true to type on successive generations.

SUMMARY OF THE INVENTION

The cultivar 'GG 6501' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG 6501.' These characteristics in combination distinguish 'GG 6501' as a new and distinct *Chrysanthemum* cultivar:

1. Large daisy type inflorescence;
2. Consistent flowering response to short days, blooming consistently after 50 to55 days of short day length;
3. Free branching habit; and
4. Bi-colored orange/yellow ray florets
5. Light green disc coloration Plants of the new cultivar 'GG 6501' are similar to plants of the parent variety, 'GG 450' in most horticultural characteristics, however plants of the new cultivar 'GG 6501' differ in the following characteristics:

1. Shorter blooming response, the new cultivar blooms consistently 3 days earlier
2. Better color retention of ray florets 3. Disc coloration is more green in the new variety
4. Better post production longevity
5. More branches produced from a pinch In comparison to the commercially available variety 'Pelee (U.S. Plant Pat. No. 8,464), 'GG 6501' differs in the following characteristics:

1. The new cultivar has a shorter blooming response by 5 days
2. The new cultivar has a more consistent ray floret coloration under high light and high temperatures
3. The cultivar is shorter by at least 5 cm when grown side by side.
4. The new cultivar produces more branches from a pinch.
5. The new cultivar has a distinctive green disc coloration, which resists changing color with aging of the plant.
6. The new cultivar has stronger lateral branches.
7. The new cultivar has a more compact plant form.

BRIEF DESCRIPTION OF THE PHOTOGRAPH

The accompanying photograph in FIG. 1 illustrates in full color a 12 week old plant of 'GG 6501' grown in a 6 inch pot. Five cuttings were used in the pot, planted mid August and grown under indoor greenhouse conditions. Day temperatures average 15 to 28 deg. C. and night temperatures average 15 to 18 deg C.

DETAILED BOTANICAL DESCRIPTION

In the following description, color references are made to The Royal Horticultural Society Colour Chart except where general terms of ordinary dictionary significance are used. The following observations and measurements describe 'GG 6501' plants grown in Oxnard, Ventura County, Calif., during the months of August through October 2004. The plants were 12 weeks old. The growing temperature ranged from 15° C. to 18° C. at night to 15° C. to 28° C. during the day. Measurements and numerical values represent averages of typical flowering types.

Botanical classification: *Chrysanthemum grandiflora* cultivar 'GG 6501.'
Commercial classification: Pot-type *Chrysanthemum.*

PROPAGATION

Time to rooting: 7 to 14 days at approximately 21° C.
Root description: Fine, fibrous.

PLANT

Growth habit: Upright, inverted triangle.
Height: Approximately 18 to 20 cm.
Plant spread: Approximately 22 to 25 cm.
Growth rate: Moderate.
Branching characteristics: Free Branching.
Length of lateral branches: Approximately 15 cm.
Number of leaves per lateral branch: Approximately 15.
Age of plant described: Approximately 60 days.

FOLIAGE

Leaf:
*Arrangement.*—Alternate single.
*Average length.*—Approximately 6.7 cm.
*Average width.*—Approximately 3.8 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.9 cm.
*Color.*—Young foliage upper side: Near Green 137C. Young foliage under side: Near Green 138B. Mature foliage upper side: Near Green 137A. Mature foliage under side: Near Green 137B.
*Venation.*—Type: Palmately net. Venation color upper side: Near Yellow-Green 146B. Venation color under side: Near Green 137D.

Petiole:
*Average length.*—Approximately 1 cm.
*Color.*—Near Green 137C.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Daisy.
*Number of inflorescences per lateral branch.*—Approximately 9.
*Inflorescence diameter.*—Approximately 9 cm.
*Inflorescence depth.*—Approximately 3 cm.
*Disc diameter.*—Approximately 1.5 cm.
*Inflorescence longevity on plant.*—Approximately 35 days.
*Persistence.*—Persistent.

Ray florets:
*Appearance.*—Matte.
*Texture.*—Smooth.
*Average number of ray florets per inflorescence.*—Approximately 350.
*Shape.*—Oblanceolate.
*Aspect.*—Flat.
*Margin.*—Entire.
*Apex.*—Obtuse.
*Length.*—Approximately 4.8 cm.
*Width.*—Approximately 1 cm.
*Color.*—Upper surface at first opening: Near Orange-Red 33A. Upper surface at maturity: Near Orange Red 34A with streaks of Yellow-Orange 14B. Upper surface at fading: Near Orange 28B with streaks of Yellow-Orange 17C. Upper surface at first opening: Near Orange-Red 34B with tips streaked with Yellow-Orange 14B. Under surface at maturity: Near Orange 28A with streaks near Yellow-Orange 15A. Under surface at fading: Near Orange-Red 30C with streaks near 15B.

Disc florets:
*Appearance.*—Shiny.
*Texture.*—Smooth.
*Average number of florets per disc.*—Approximately 350.
*Shape.*—Cylindric.
*Apex.*—Obtuse.
*Average length.*—Approximately 0.8 cm.
*Average width.*—Approximately 0.1 cm.
*Color.*—At first opening: Near Green 143B. At maturity: Near Green 143C. At fading: Near Yellow-Green 154B.

Peduncle:
*Length.*—At terminal end (shortest): Approximately 4.2 cm. At lateral end (longest): Approximately 6.9 cm.
*Angle to stem.*—Acute.
*Strength.*—Moderate.
*Color.*—Near Green 137B.
*Habit.*—Upright.
*Diameter.*—0.3 cm.
*Surface texture.*—Lightly pubescent.

Inflorescence bud:
*Length.*—Approximately 1 cm.
*Diameter.*—Approximately 1 cm.
*Form.*—Globular.
*Color.*—Near Yellow 6B.

Involucral bracts (phyllaries):
*Appearance.*—Matte.
*Texture.*—Lightly pubescent.
*Number.*—Approximately 35.
*Shape.*—Ovate.
*Margin.*—Entire.
*Apex.*—Acute.
*Length.*—0.8 cm.
*Width.*—0.9 cm.
*Color.*—Upper side: Near Green 137B. Under side: Near Green 137B.

REPRODUCTIVE ORGANS

Ray florets:
*Number of pistils per floret.*—1.
*Stigma shape.*—2 branched.
*Stigma color.*—Near 15A.
*Style color.*—Near Yellow 7A.
*Style length.*—Approximately 1 cm.
*Stamens.*—Absent.

Disc florets:
*Number of pistils per floret.*—1.
*Stigma shape.*—Cylindric.
*Stigma color.*—Near 154A.

*Style length.*—Approximately 0.2 cm.
*Style color.*—Near Yellow-Green 154A.
*Number of stamens per floret.*—Approximately 5.
*Anther shape.*—Tubular.
*Anther color.*—Near Yellow 2A.
*Pollen color.*—Near Yellow 6A.

OTHER CHARACTERISTICS

Disease resistance: Neither resistance nor susceptibility to diseases or pests has been observed in this variety.

Drought tolerance/cold tolerance: The new cultivar has only been observed under indoor conditions, therefore drought and cold tolerance have not been observed.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG 6501' as illustrated and described.

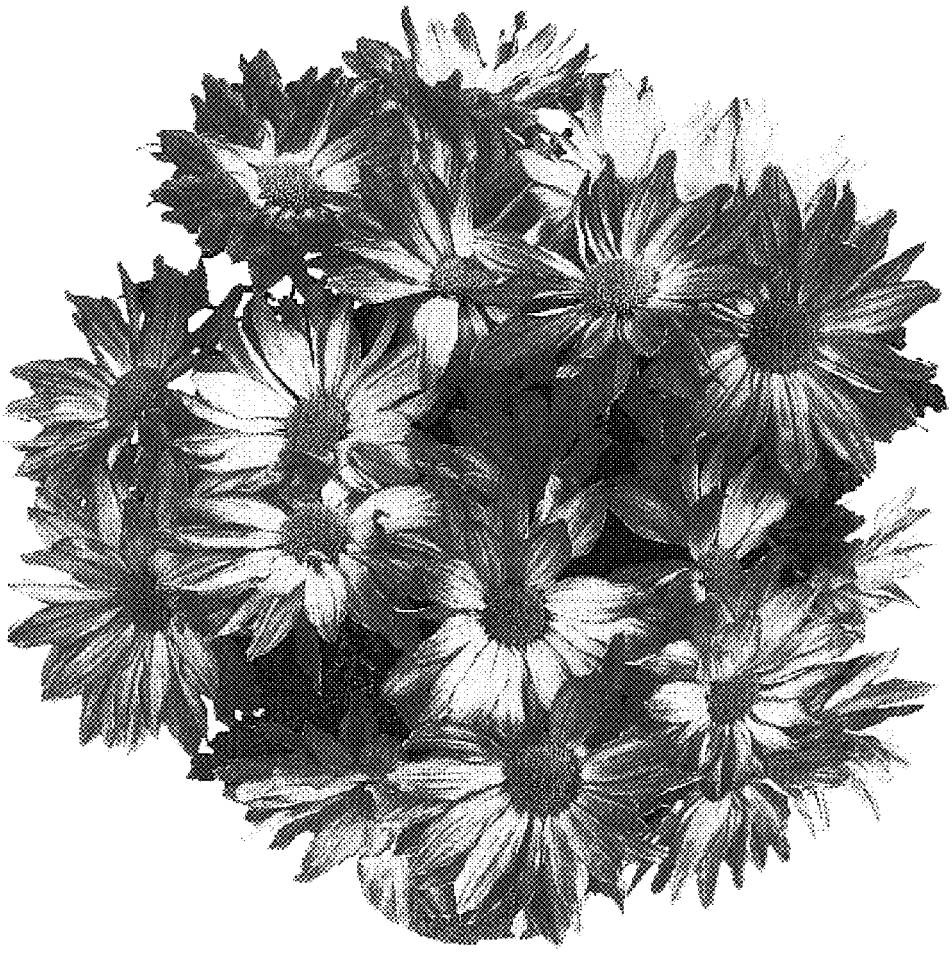

* * * * *